United States Patent [19]
Holschbach et al.

[11] Patent Number: 5,312,446
[45] Date of Patent: May 17, 1994

[54] COMPRESSED STORAGE OF DATA IN CARDIAC PACEMAKERS

[75] Inventors: Jean M. Holschbach, Circle Pines; Lucy M. Nichols, Maple Grove; David L. Thompson, Fridley, all of Minn.

[73] Assignee: Medtronic, Inc., Minneapolis, Minn.

[21] Appl. No.: 935,953

[22] Filed: Aug. 26, 1992

[51] Int. Cl.$^5$ ............................................. A61N 1/00
[52] U.S. Cl. .......................................... 607/9; 607/14; 607/30
[58] Field of Search ...................... 128/419 PG, 419 D

[56] References Cited

U.S. PATENT DOCUMENTS

| | | | |
|---|---|---|---|
| 4,223,678 | 9/1980 | Langer et al. | 128/419 D |
| 4,295,474 | 10/1981 | Fischell | 128/697 |
| 4,407,288 | 10/1983 | Langer et al. | 129/419 PG |
| 4,407,296 | 10/1983 | Anderson | 128/675 |
| 4,485,813 | 12/1984 | Anderson et al. | 128/675 |
| 4,556,063 | 12/1985 | Thompson et al. | 128/419 PT |
| 4,625,730 | 12/1986 | Fountain et al. | 128/419 D |
| 4,729,376 | 3/1988 | DeCote, Jr. | 128/419 PT |
| 4,800,883 | 1/1989 | Winstrom | 128/419 D |
| 4,858,610 | 8/1989 | Callaghan et al. | 128/419 PG |
| 4,878,497 | 11/1989 | Callaghan et al. | 128/419 PG |
| 5,127,404 | 7/1992 | Wyborny et al. | 128/419 P |

OTHER PUBLICATIONS

Thomas J. Lynch, Ph.D., Data Compression Techniques and Applications, Van Nostrand Reinhold Company, New York, pp. 256-259.

Edited by Barold et al., "Memory Technology and Implantable Holter Systems", Advances in Technology and Clinical Applications: The Third Decade of Cardiac Pacing, Chapter Three, Part IV, Futura Publishing Company, Mount Kisco, N.Y., 1982.

*Primary Examiner*—William E. Kamm
*Assistant Examiner*—Scott M. Getzow
*Attorney, Agent, or Firm*—Harold R. Patton

[57] ABSTRACT

An implantable medical device for human implant. The device includes a telemetry transmitter and receiver for communicating information from the implanted device to an external programmer or monitor and for receiving commands or other information from an external programmer. The device is provided with one or more sensors and means for monitoring, recording and storing the recordings of physiologic signals after implant. The device is provided with a waveform compression and storage system which stores monitored signals in the form of defined analog voltages maintained within the device, rather than employing more traditional digital storage techniques.

19 Claims, 10 Drawing Sheets

COMPRESSED STORAGE OF DATA IN CARDIAC PACEMAKERS

FIELD OF THE INVENTION

This invention relates generally to the field of cardiac pacemakers, and more particularly relates to the compression and storage of analog signals therein.

BACKGROUND OF THE INVENTION

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiological based signals, such as signals from sensors for measuring the pressure inside the patient's ventricle or measuring the level of the patient's physical activity. These are labeled "VVIR" for a single chamber version or "DDDR" for a dual chamber version.

The complexity of modern pacemakers, the occurrence of rare device failures, or, more commonly, physiologic changes, and device variables or drift dictate the need for numerous programmable parameters accessible noninvasively via an externally operated programmer. The need to assess system performance or troubleshoot the patient, device and/or lead system in an acute, clinical setting or long-term, while the patient is ambulatory, is increasing.

Ambulatory EKG monitoring is the most effective way of determining satisfactory pacemaker or cardioverter/defibrillator function. In the presence of a malfunction that has occurred or has been provoked by daily activity, there is no technique that provides better accuracy for determination of the state of the function of the implanted device and its interaction with the patient. Passive EKG monitoring with provocative testing, can frequently detect a malfunction of the implanted device and is the basic technique utilized today. Additionally, the storage of data in counters or, more recently, rate or trend histograms, and the use of telemetry markers to indicate device function may aid in the diagnosis of malfunction or may allow optimization of device performance. However, it is often impossible in an acute, clinical setting to duplicate specific daily events and activities, thus many problems are unresolved. Additionally, it is impossible to record for prolonged periods of time and even for short periods of time with adequate resolution. Lastly, event counters and histograms do not provide the temporal relationship between events to enable diagnosis of transiently occurring problems.

Episodic events such as transiently brief runs of pacemaker mediated tachycardia (PMT), supraventricular tachycardia (SVT) or syncope can be detected as a source of clinically significant symptoms by ambulatory monitoring and rarely occur during clinical passive EKG evaluation. Events related to daily activity, electromagnetic interference (EMI), loss of capture via specific body position or activity, and the effect of sleep or activity on patient/device interaction may be readily demonstrated by ambulatory monitoring.

However, ambulatory "holter" monitoring typically entails attaching tape-on electrodes to a patient and monitoring the surface EKG via a tape recorder or integrated circuit (IC) memory recorder worn on the patient's belt for a 24-hour period. This "strapped on" device causes patient discomfort and limits activity. If the transient event is not captured, the trial must be repeated or the troubleshooting process must be curtailed or changed to a trial and error method for problem resolution. Additionally, the evaluation of the 24 hours of stored data is a time intensive and expensive process. Lastly, standard holter monitoring has no capability for determining device function simultaneous with the stored EKG artifacts.

Devices have been proposed for the electronic storage and transmission of the analog information in an implantable medical device to solve the above listed problems and shortcomings. The most common method is to digitize (i.e. change to digital format) an analog signal for storage or transmission. For example, U.S. Pat. No. 4,223,678 by Langer, et al., discloses the recording of EGM data prior to and following the detection of an arrhythmic event and subsequentially delivered shock. Pre-event analog data is converted by an analog to digital converter (ADC) and stored in auxiliary memory while post-event data is stored in main memory. Both memories are frozen upon storing of the single episodic event.

U.S. Pat. No. 4,407,288 by Langer, et al., discloses a two micro-processor based implantable defibrillator with ECG recording capability. Pre-event detection data is stored via a low speed processor into memory via direct memory access (DMA). Upon event detection, the data for a single event is frozen.

U.S. Pat. No. 4,625,730 by Fountain, et al., discloses the storage of ECG data via DMA to memory. One event may be stored for a total time duration of 10.24 seconds. Also, the '730 patent discloses a hand-held patient programmer used as an actuator to trigger the storage of an event.

U.S. Pat. No. 4,295,474 by Fishell discloses the recording of ECGs as in the '678 patent along with the recording of time and number of arrhythmic episodes since the previous office visit. The ECG is converted by a six bit ADC at 50 Hz for the storage and memory of one event for a total duration of 80 seconds. Ten seconds of continuously stored data is contained in a section of memory to enable the freezing and storage of 10 seconds of pre-event data and 70 seconds of post-event data.

The prior art listed above may be typically characterized by digitizing data with an ADC, the storage of a single event with limited duration (10–80 seconds), no provision for extended storage times or storage of multiple events/episodes, generally low fidelity signals, and extended telemetry transmission times to external peripherals.

To obtain extended storage capability (long storage time or multiple storage of events), digitized analog signals, such as an ECG, would require very large memory storage capability—140 million bits of memory per day—(see Chapter 1, Part 4 "The Third Decade of Cardiac Pacing"). Memory of that size would require a large number of integrated circuits and would not fit in a typically sized implantable pulse generator, would cause excessive current drain from the battery during operation and require nearly five hours to uplink to a peripheral utilizing a "state-of-the-art" telemetry system. Proposed solutions to the large amount of memory required include data reduction techniques such as blanking out all signals except for the signals indicative of the atrial and ventricular depolarization and repolarization (PQRST interval) which is then converted via standard techniques. This results in a reduction of the storage requirements of only approximately 50 percent. Additionally, compression techniques such as Coordinate-Reduction-Time-Encoding-System (CORTES) or Amplitude-Zone-Epoch-Time-Coding (AZTEC) may be used to achieve up to 10:1 data compression (see Data Compression—Techniques and Applications, Pg. 256-259, T. J. Lynch). However these techniques are not suitable for use in implantable medical devices because of the extensive processing power required to compress and store data real time.

Additionally, data stored in an implantable medical device's volatile memory can be erased or contaminated (flawed) by device failure, EMI, cautery or defibrillation procedures. Therefore, most implantable pulse generators have a power-on reset (POR) circuit that resets memory when power supply glitches occur. Any stored data is then erased and lost to the follow-up clinician.

Alternative methods proposed for the storage of analog signals in implantable pulse generators include magnetic bubble memories (see Chapter 3, Part 4 "The Third Decade of Cardiac Pacing") and Charge Coupled Devices (CCD). Present problems with bubble memories include the limited size of the memory (or alternatively, the large size of the integrated circuit), the difficulty in the read/write mechanism required and the complexity of the interface circuitry to the rest of the implantable pulse generator circuit (typically constructed of CMOS circuitry). Alternatively, in a CCD, the signal to be recorded is stored as a charge on an integrated capacitor. However analog information cannot be stored on a CCD for very long because the capacitor leakage rate on the CCD is too high to maintain accuracy for any significant length of time.

What is needed is a device that can electrically store analog information in an implantable medical device with reasonable precision, for long terms, with substantially reduced complexity, minimized current drain from the battery, greatly reduced memory requirements, increased telemetry transmission rates and the integration of signals marking specific function of the implanted device simultaneous with the recording of the analog signal. The system of the present invention provides for an efficient electronic recording and playback system for an implantable medical device which stores signal information in considerably less memory, with reduced complexity, and reduced current drain than that required for digital storage, and includes markers indicative of device function.

SUMMARY OF THE INVENTION

It is, therefore, an objective of the present invention to provide an apparatus for placing and storing analog data into nonvolatile memory of an implantable medical device.

It is furthermore an objective of the present invention to compress the analog data prior to storage, whereby less memory is required. Adequate fidelity for clinical use is maintained during the compression operation.

It is furthermore an objective of the present invention to provide for the transmission of the analog data to an external peripheral for subsequent clinical use.

It is furthermore an objective of the present invention to incorporate signals indicative of implanted device function interleaved with the stored analog data.

It is furthermore an objective of the present invention to utilize the stored analog data to enable arrhythmia detection and treatment.

It is furthermore an objective of the present invention to utilize the stored analog data to enable the detection of an evoked response in an auto capture mode of operation.

The above and other objectives that will herein after appear, and the nature of the invention, will more clearly be understood by reference to the following description, the amended claims and the accompanying drawings.

DESCRIPTION OF THE DRAWINGS

The foregoing and other features of the present invention will be best appreciated with reference to the detailed description of a specific embodiment of the invention, which follows, read in conjunction with accompanying drawings wherein.

DETAILED DESCRIPTION OF SPECIFIC EMBODIMENTS OF THE INVENTION

Figure 1:
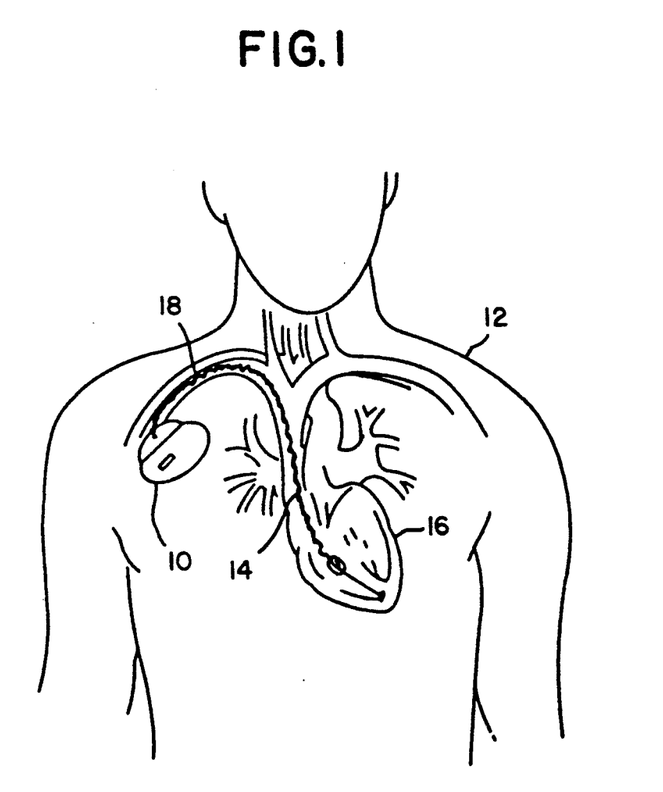
FIG. 1 is a diagram showing the placement in a patient of a pacemaker in accordance with the present invention.

The present invention will now be more fully described with reference to the various Figures of the drawings, FIG. 1 showing generally how a pacemaker 10 in accordance with the present invention may be implanted in a patient 12. A pacemaker lead 14 is electrically coupled to pacemaker 10 and extends into the patient's heart 16 via a vein 18. The distal end of lead 14 includes one or more exposed conductive electrodes for receiving electrical cardiac signals and for delivering electrical pacing stimuli to the patient's heart 16. In accordance with the invention to be hereinafter described, the distal end of pacemaker lead 14 may also incorporate a pressure transducer (not shown in FIG. 1 due to the small scale of that Figure) for producing electrical signals representative of the pressure inside heart 16.

Figure 2:
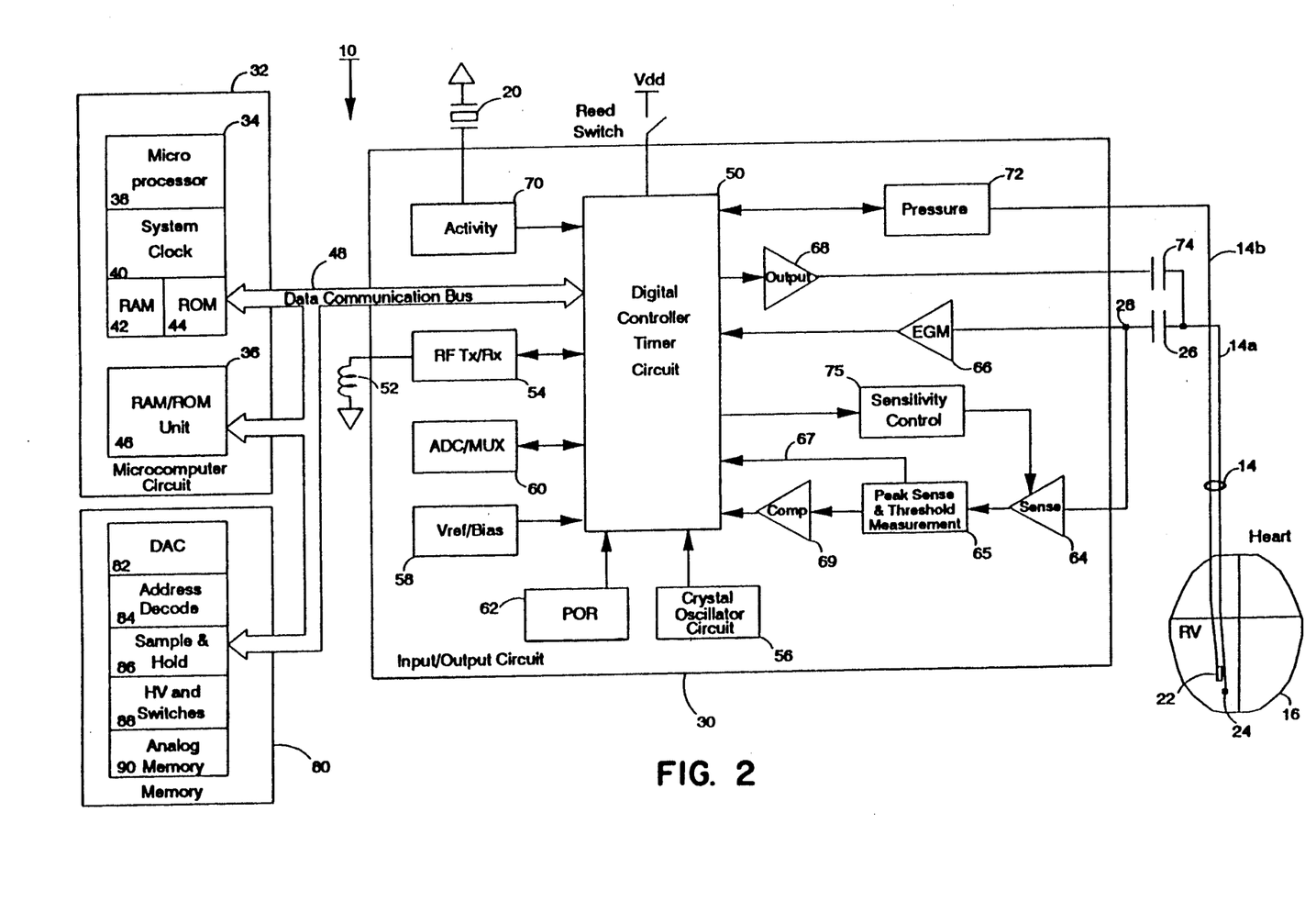
FIG. 2 is a block diagram of the circuitry of a pacemaker in accordance with one embodiment of the present invention.

Turning to FIG. 2, a block diagram of pacemaker 10 from FIG. 1 is shown. Although the present invention is described in conjunction with a pacemaker 10 having a microprocessor-based architecture, it will be understood that it could be implemented in any logic based, custom integrated circuit architecture, if desired. It will also be understood that the present invention may be utilized in conjunction with other implantable medical devices, such as cardioverters, defibrillators, neural stimulators, cardiac assist systems, and the like.

In the embodiment shown in FIG. 1, pacemaker 10 includes an activity sensor 20, which may be, for example, a piezoelectric element bonded to the inside of the pacemaker's housing. Sensor 20 provides a sensor output which varies as a function of a measured parameter that relates to the metabolic requirements of patient 12. In addition, pacemaker 10 includes a pressure sensor 22 disposed at the distal end of lead 14, as previously noted, which may be similarly used to ascertain the metabolic requirements and/or cardiac output of patient 12. Pressure sensor 22 may be a piezoelectric element such as is disclosed in U.S. Pat. No. 4,407,296 to Anderson, entitled "Integral Hermetic Implantable Pressure Transducer," or U.S. Pat. No. 4,485,813 to Anderson et al., entitled "Implantable Dynamic Pressure Transducer System," each assigned to the assignee of the present invention and incorporated herein by reference.

Pacemaker 10 is schematically shown in FIG. 2 to be electrically coupled via a pacing lead 14 to a patient's heart 16. Lead 14 includes an intracardiac electrode 24 and pressure sensor 22 located near its distal end and positioned within the right ventricular (RV) chamber of heart 16. Lead 14 can carry either unipolar or bipolar electrodes as is well known in the art. In the presently disclosed embodiment, lead 14 which couples pacemaker 10 to the ventricula endocardium can comprise a steroid-tipped, unipolar lead with an integral pressure transducer of the type described in the aforementioned references. Electrode 24 is coupled via suitable lead conductor 14a through input capacitor 26 to node 28 and to input/output terminals of an input/output circuit 30. Output from first sensor 20 is coupled to input/output circuit 30. Output from pressure sensor 22 is also coupled to input/output circuit 30 via suitable lead conductor 14b.

Input/output circuit 30 contains the analog circuits for interface to the heart 16, activity sensor 20, pressure sensor 22, and antenna 52, as well as for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. Off-board circuit 36 includes an off-board RAM/ROM unit 46. Microcomputer circuit 32 is coupled by data communication bus 48 to a digital controller/timer circuit 50. Microcomputer circuit 32 may be fabricated of custom integrated circuit devices augmented by standard RAM/ROM components. Data communication bus 48 is also coupled to an analog memory integrated circuit 80 which includes a DAC 82, an address decode circuit 84, a sample and hold circuit 86, a high voltage supply and associated switches 88 and EEPROM memory cells 90.

It will be understood that the electrical components represented in FIG. 2 are powered by an appropriate implantable battery power source, not shown, in accordance with common practice in the art.

An antenna 52 is connected to input/output circuit 30 for purposes of uplink/downlink telemetry through RF transmitter/receiver (RF TX/RX) unit 54. Telemetering both analog and digital data between antenna 52 and an external device, such as an external programmer (not shown), is accomplished in the presently disclosed embodiment by means of all data first being digitally encoded and then pulse-position modulated on a damped RF carrier, as substantially described in co-pending U.S. patent application Ser. No. 07/468,407, filed on Jan. 22, 1990, entitled "Improved Telemetry Format," which is assigned to the assignee of the present invention and which is incorporated herein by reference.

A crystal oscillator circuit 56, typically a 32,768-Hz crystal-controlled oscillator, provides main timing clock signals to digital controller/timer circuit 50. A Vref/Bias circuit 58 generates a stable voltage reference and bias currents for the analog circuits of input/output circuit 30. An analog-to-digital converter/multiplexor (ADC/MUX) unit 60 digitizes analog signals and voltages to provide "real-time" telemetry of pressure and intracardiac signals and battery end-of-life (EOL) replacement function. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input/output circuit 30.

Digital controller/timer circuit 50 is coupled to a sense amplifier 64 and an electrogram amplifier 66 for receiving amplified and processed signals picked up from electrode 24 through lead conductor 14a and capacitor 26 representative of the electrical activity of the patient's heart 16. Sense amplifier 64 amplifies sensed electrical cardiac signals and provides this amplified signal to peak sense and threshold measurement circuitry 65, which provides an indication of peak sensed voltages and the measured sense amplifier threshold voltage on multiple conductor signal path 67 to digital controller/timer circuit 50. The amplified sense amplifier signal is also provided to a comparator 69. The electrogram signal developed by EGM amplifier 66 is used in those occasions when the implanted device is being interrogated by an external programmer, not shown, in order to transmit by uplink telemetry a representation of the analog electrogram of the patient's electrical heart activity as described in U.S. Pat. No. 4,556,063, issued to Thompson et al., assigned to the assignee of the present invention and incorporated herein by reference. An output pulse generator 68 provides the pacing stimulus to the patient's heart 16 through coupling capacitor 74 in response to a pacing trigger signal developed by digital controller/timer circuit 50 each time the escape interval times out, or an externally transmitted pacing command has been received, or in response to other stored commands as is well known in the pacing art.

Digital controller/timer circuit 50 is coupled to an activity circuit 70 for receiving, processing, and amplifying signals received from activity sensor 20. Activity circuit 70 produces an activity signal which is representative of the patient's metabolic requirements. Similarly, digital controller/timer circuit 50 is coupled to a pressure circuit 72 for receiving, amplifying and processing sensor output from pressure sensor 22. In the presently disclosed embodiment of the invention, pressure circuit 72 produces an amplified, filtered analog pressure signal which is received by digital controller/timer circuit 50. In conjunction with ADC/MUX 60, digital controller/timer circuit samples and digitizes the pressure signal from pressure circuit 72 to obtain a digital representation of the peak value of intracardiac pressure during each cardiac cycle. This value is provided to microprocessor 34, which maintains a running average over a previous number of cardiac cycles (e.g. sixteen) of the intracardiac pulse pressure.

With continued reference to FIG. 2, input/output circuit 30 further includes sensitivity control circuitry 75 coupled between digital controller/timer circuit 50 and sense amplifier circuit 64. Sensitivity control circuit 75 controls the sense amplifier gain and thus the sensing threshold of sense amplifier 64 as instructed by digital controller/timer circuit 50.

With reference to memory 80 of FIG. 2, digital to analog converter (DAC) 82 converts a digital representation of a signal into an analog signal. Address decode 84 controls the addressing of the row and column of analog memory 90 for both writing and reading data. Sample and hold circuit 86 samples an analog signal at a periodic rate to enable the storage of an analog signal in analog memory 90. High voltage (HV) and switch circuit 88 generates an approximate 20 volt DC voltage and, via the switches, stores a representation of an analog signal in analog memory 90. Analog memory 90 is a standard EEPROM memory utilized in this application to store analog signals.

Figure 3:
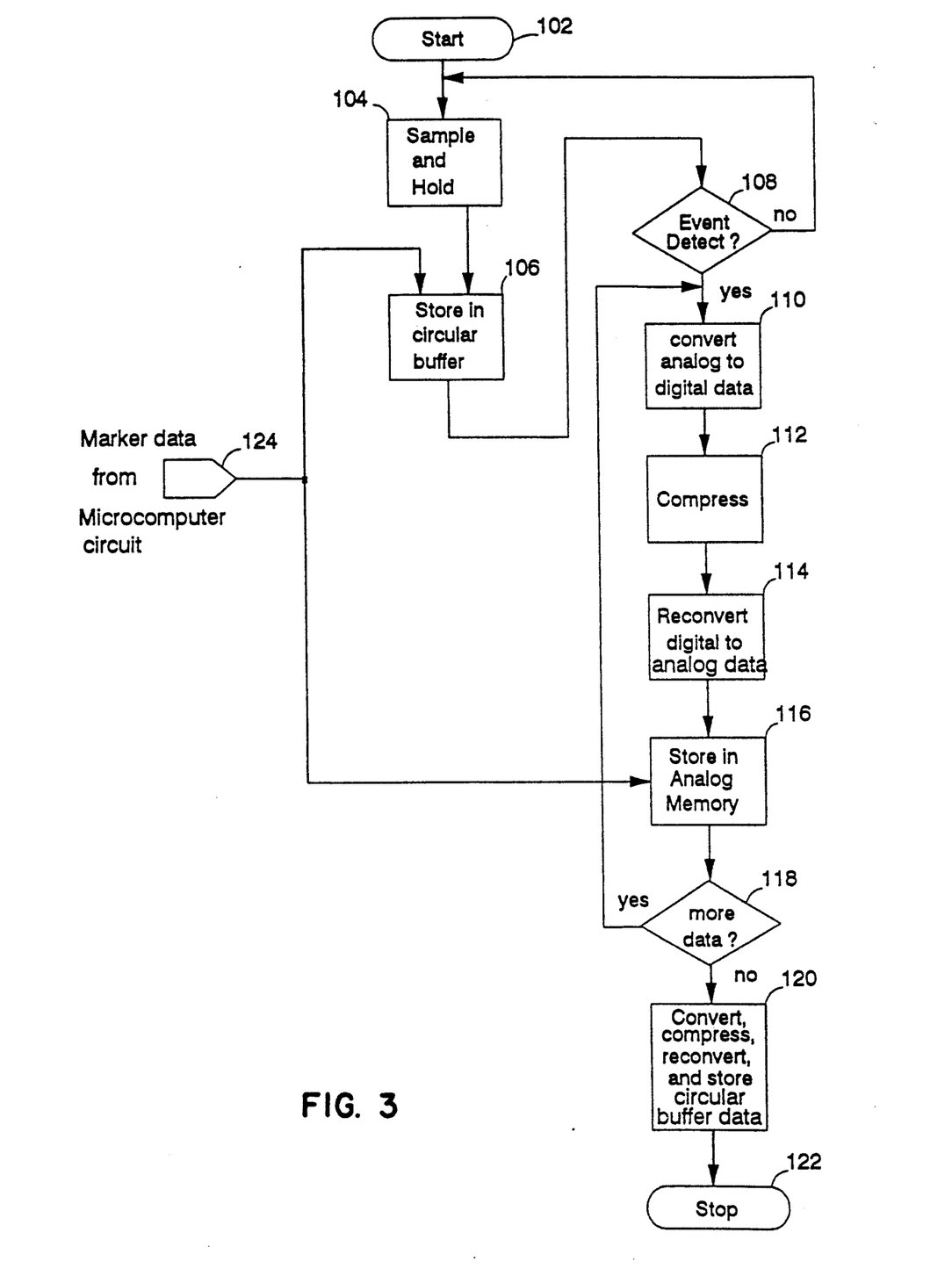
FIG. 3 is a flow diagram illustrating a mode of operation of the pacemaker of FIG. 2.

Turning now to FIG. 3, the preferred embodiment for the compression and storage of an analog signal in the pacemaker of FIG. 2 is shown. The signal to be stored may be one or both of the intracardiac signal from the EGM amplifier 66 of FIG. 2 and/or a signal from a sensor such as the pressure sensor 22 shown in FIG. 2. The EGM amplifier 66 and pressure circuit 72 amplify and filter the appropriate physiologic signal from the patient and provide a voltage level suitable for storing in memory 80. The flow diagram of FIG. 3 is initiated at block 102. The data to be stored is sampled and held at block 104 by sample and hold circuit 86 of FIG. 2. At block 106, the data is stored in a section of analog memory 90 via address decode 84 and high voltage supply (HV) and switch circuit 88, all of FIG. 2.

Digital data indicative of device function may also be stored interdispersed among the analog signal as herein described later in association with FIGS. 9 and 10. Analog memory 90 may be of the type incorporated in ISD 1016, a telecommunication monolithic integrated circuit from Information Storage Devices, Inc. A preliminary specification dated March, 1991 is incorporated herein by reference in its entirety. Analog data is continuously stored in a circular buffer (a section of analog memory 90), enabling 30 seconds of pre-event data to be frozen upon an event detection period.

Automatic event detection is tested for in block 108 by microcomputer circuit 32 of FIG. 2 which monitors the intracardiac electrogram for arrhythmias, PVCs or runs of PVCs, as shown in co-pending U.S. patent application Ser. No. 07/881,996, filed on May 1, 1992 entitled "Diagnostic Function Data Storage and Telemetry Out for Rate Responsive Cardiac Pacemaker," and assigned to the assignee of the present invention and incorporated herein by reference in its entirety. Alternatively, patient activation by reed switch closure with a hand-held magnet placed over the implant site may also trigger storage of signals. Upon automatic detection of the event, or patient activation, the analog data is converted to digital data at block 110 by 8 bit ADC 60 of FIG. 2. During the data compression process, the sample and hold 104 and storage in buffer 106 are bypassed and the analog data is compressed in real-time. At block 112, the digital data is compressed as will herein below be described. The compressed data is reconverted to analog voltage levels at block 114 via DAC 82 of FIG. 2. At block 116 the marker data from the microcomputer 32 and the reconverted data from block 114 are stored in analog memory 90 via address decode 84 and high voltage supply (HV) and switch circuit 88, all of FIG. 2. A test for 2 more data values is evaluated at block 118. If 'YES', the flow diagram returns to block 110. If 'NO', the flow diagram moves to block 120 where data temporarily stored in a section of analog memory 90 used as a circular buffer is converted, compressed, reconverted and stored as herein described above. Upon completion of storage of the data temporarily stored in the circular buffer, the flow diagram exits at block 122.

In the present embodiment, five minutes of data may be stored along with the 30 seconds of pre-event data from the circular buffer and the time of occurrence from a system clock from microcomputer circuit 32 of FIG. 2. Nine separate events including pre-event, post-event and time of occurrence of each may be stored in an ISD 1016 (a 128K byte) analog memory 80. More or longer episodes may be stored if larger memory capacity or multiple integrated circuits are available. Memory 80 may operate in a freeze mode whereupon being filled with nine separate events, the data is frozen under command of microcomputer 32 until interrogation and reset by an external programmer, not shown. Alternatively, memory 80 may operate in a circular buffer or overwrite mode whereby the most recent nine events will be stored in memory and may be read and reviewed by a clinician upon interrogation by the programmer. In either storage mode, the external programmer may reset and reinitiate the storage function under program commands as is well known in the art. The reading of the stored data from analog memory 90 is under control of microcomputer 32, address decode 84 and high voltage and switch circuit 88 whereby a specific memory bit is addressed and the analog signal is reconstructed sequentially, one bit at a time. This signal is routed through bus 48 to input/output circuit 30 for transmission to an external programmer (not shown) via RF transmit/receive circuit 54 and antenna 52.

It should be apparent that other methods of patient activation may be used such as tapping on the pacemaker can with a signal generated by the activity sensor 20 of FIG. 2 being detected to trigger the recording episode. Additionally, a simple patient programmer may be utilized to trigger the storage event.

Figure 4:
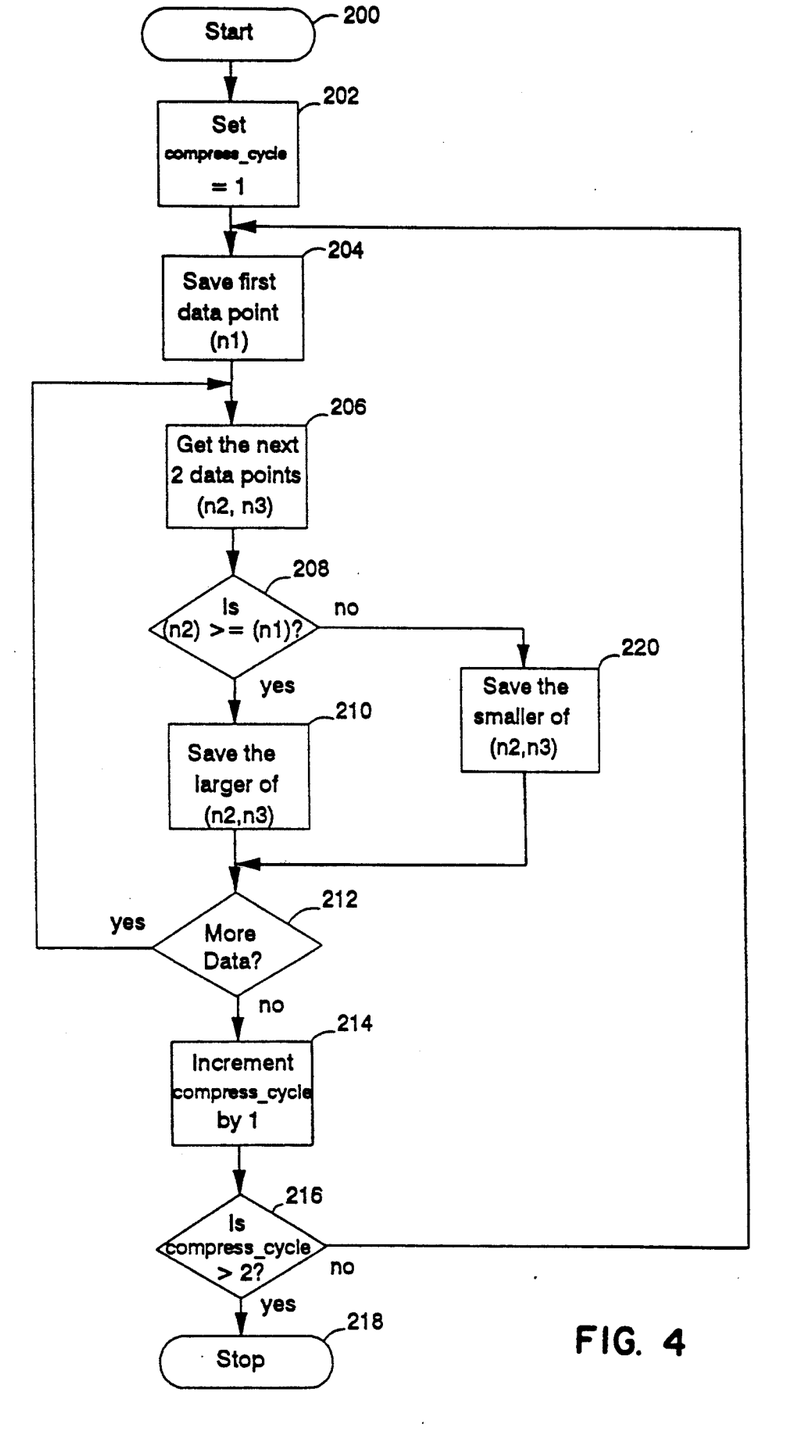
FIG. 4 is a flow diagram further illustrating the mode of operation of the pacemaker of FIG. 2.

Turning now to FIG. 4, a flow diagram is shown which illustrates the compression process 110 of FIG. 3 in accordance with the presently disclosed embodiment of the invention. The flow diagram of FIG. 4 begins with the starting of the compression process at block 200 by event detection 104 of FIG. 3. At block 202 a counter, COMPRESS_CYCLE, is set to 1. The first voltage value data point ($n_1$) is saved at block 204. The following two data points, $n_2$ and $n_3$, are obtained in block 206 from block 110 of FIG. 3. Data point $n_2$ is compared to the saved data point $n_1$ at block 208. If $n_2$ is equal to, or greater than, $n_1$, block 208 returns a 'YES' and the larger of $n_2$ or $n_3$ is saved at block 210. If $n_2$ is smaller than $n_1$, then the smaller of $n_2$ or $n_3$ is saved at block 220. More data is tested for at block 212. If at least 2 more data values are available, the flow diagram returns to block 206. If block 212 returns a 'NO', the COMPRESS_CYCLE counter is incremented by 1. At block 216, if the COMPRESS_CYCLE counter is greater than 2 the flow diagram is exited at block 218. If the COMPRESS_CYCLE counter is less than, or equal to 2 the flow diagram returns to block 204. As described in this preferred embodiment, the flow diagram is serially repeated a second time on the data compressed and stored by the algorithm of FIG. 4 to enable the compression of data by a factor of 4 to 1. The flow diagram of FIG. 4 retains good fidelity by storing the maximum or minimum transition points in a waveform while reducing the stored data by 75%.

Figure 5:
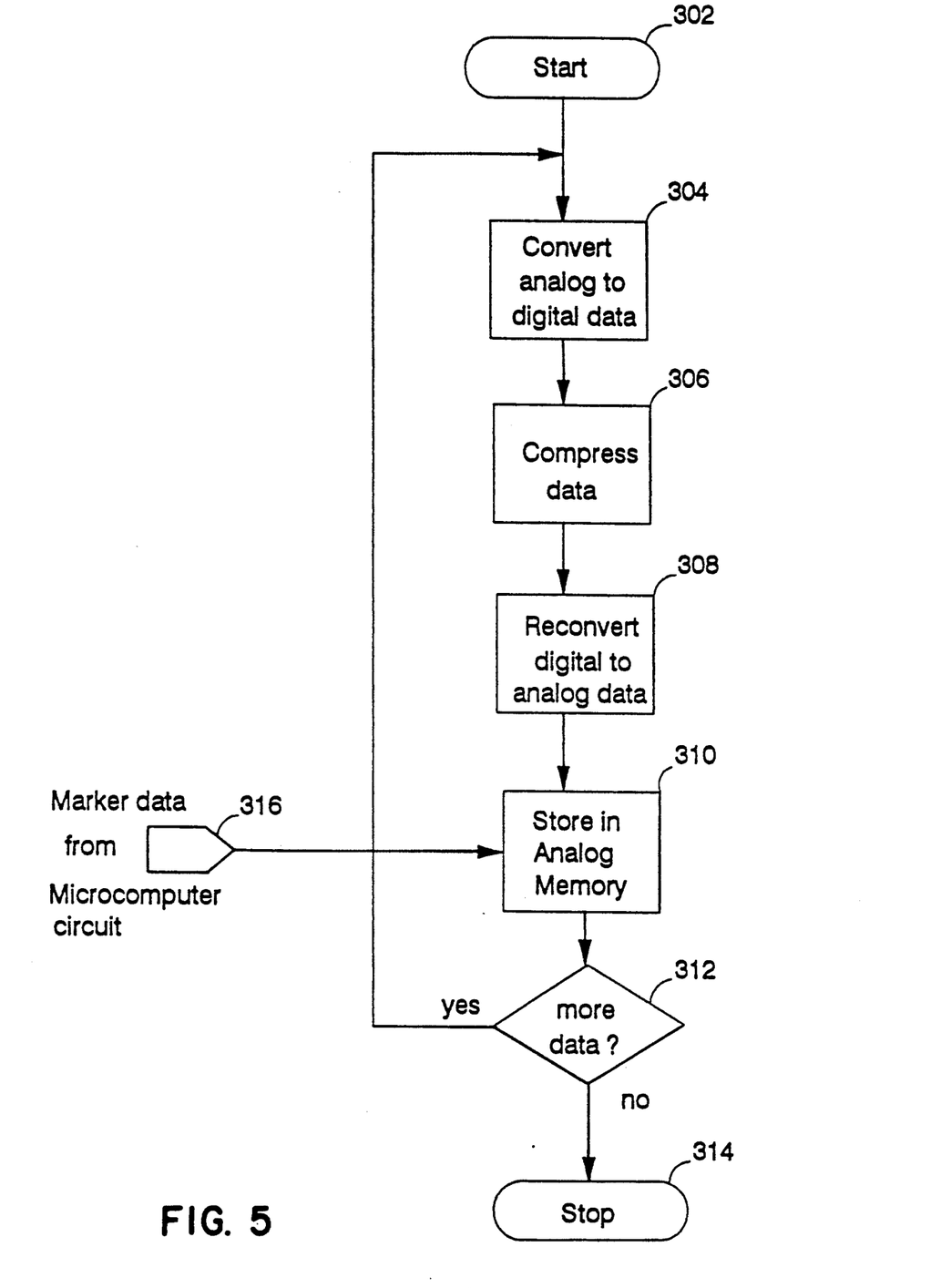
FIGS. 5 and 6 are flow diagrams with alternative modes of operation of the pacemaker of FIG. 2.

Turning now to FIG. 5, a flow diagram is shown which illustrates an alternative embodiment whereby the implantable device 10 of FIG. 1 incorporates an implantable 24 hour holter monitor. The signal to be stored may be one or both, the intracardiac signal from EGM amplifier 66 of FIG. 2 and/or the signal from a sensor such as the pressure sensor 22 shown in FIG. 2. The flow diagram is initiated at block 302 by the methods as herein described above (e.g. event detection, programming or patient activation). The analog signal is converted to a digital word in block 304 via the 8-bit ADC 60 of FIG. 2. At block 306, the data is compressed via the technique as described herein above and shown in FIG. 4. At block 308, the compressed digital data is reconverted to voltage levels via the DAC 82 shown in FIG. 2. At block 310, the marker data from the microcomputer circuit 32 of FIG. 2 and the reconverted data from block 308 are stored in analog memory 90 of FIG. 2. A test for more data is evaluated at block 312. If 'YES', the flow diagram returns to block 304. If 'NO', the flow diagram exits at block 314. Block 310 may store data in a freeze mode or an over-write mode under control of microcomputer 32, FIG. 2.

Figure 6:
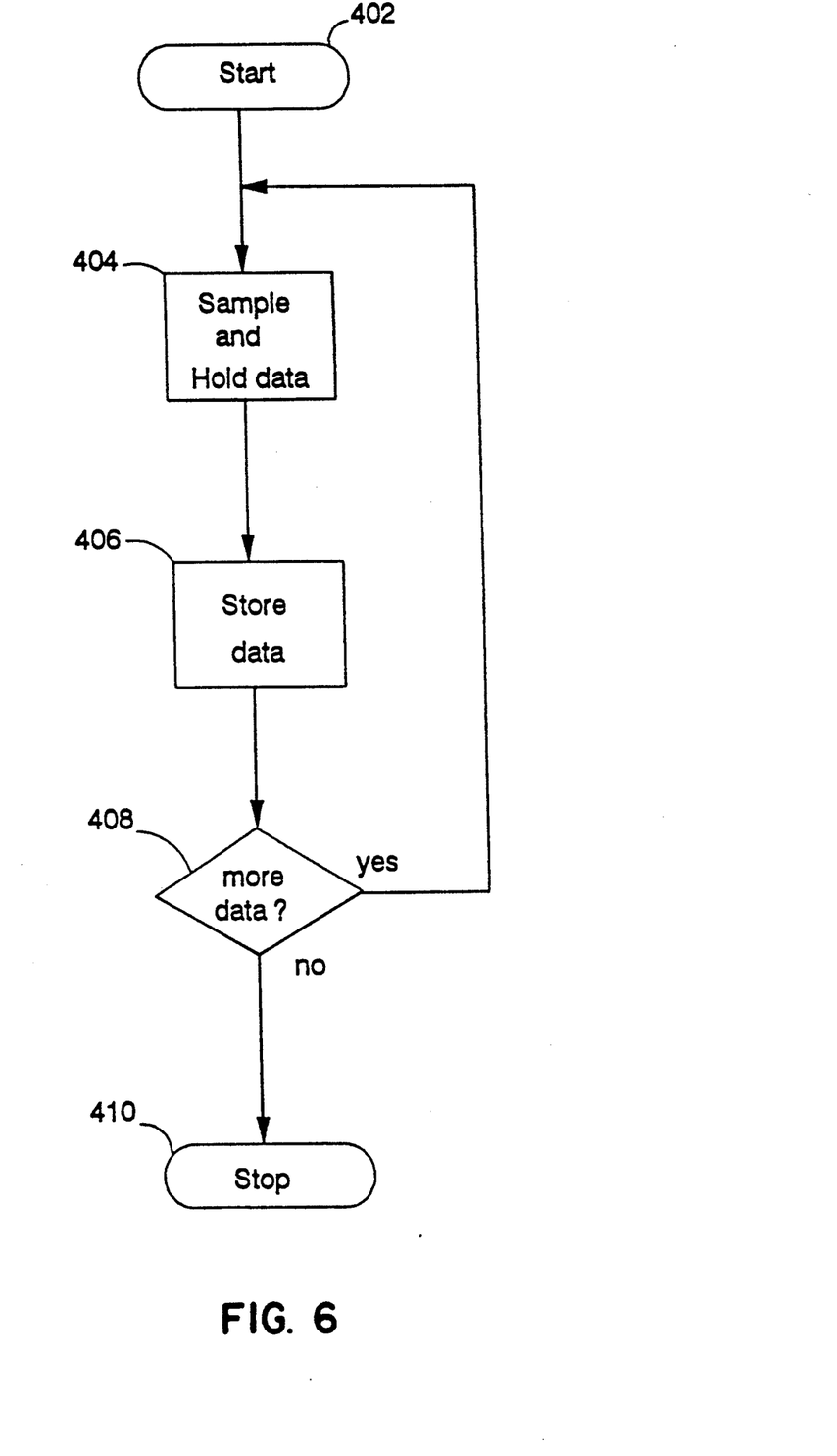

Referring now to FIG. 6, a flow diagram is shown which illustrates an alternative embodiment whereby the implantable device 10, FIG. 1, incorporates storage of analog EGM data directly without an intervening conversion to digital data and subsequent reconversion to analog data. The signal to be stored may be one or both, the intracardiac signal from EGM amplifier 66 of FIG. 2 and/or the signal from a sensor such as the pressure sensor 22 shown in FIG. 2. The flow diagram is initiated at block 402 by the methods as described herein above (e.g. event detection, programming or patient activation). The analog data is sampled and held at block 404 by a sample and hold circuit 86 of FIG. 2. The sampling may occur at a 128 Hz rate for adequate clinically useful data. At block 406, the data is stored in analog memory 90 via address control 84 and high voltage supply (HV) and switches 88 of FIG. 2. At block 408, a test for more data is entered. If 'YES', the flow diagram returns to sample and hold block 404. If 'NO', the flow diagram is exited at block 410. This embodiment is simpler, requires less circuitry and less current drain from the battery because of the elimination of the analog to digital conversion 304, the compression of data 306 and the digital to analog conversion 308 from FIG. 5. The embodiment shown in FIG. 6 will have improved fidelity and will compress data to 8:1 versus a digital equivalent.

Figure 7:
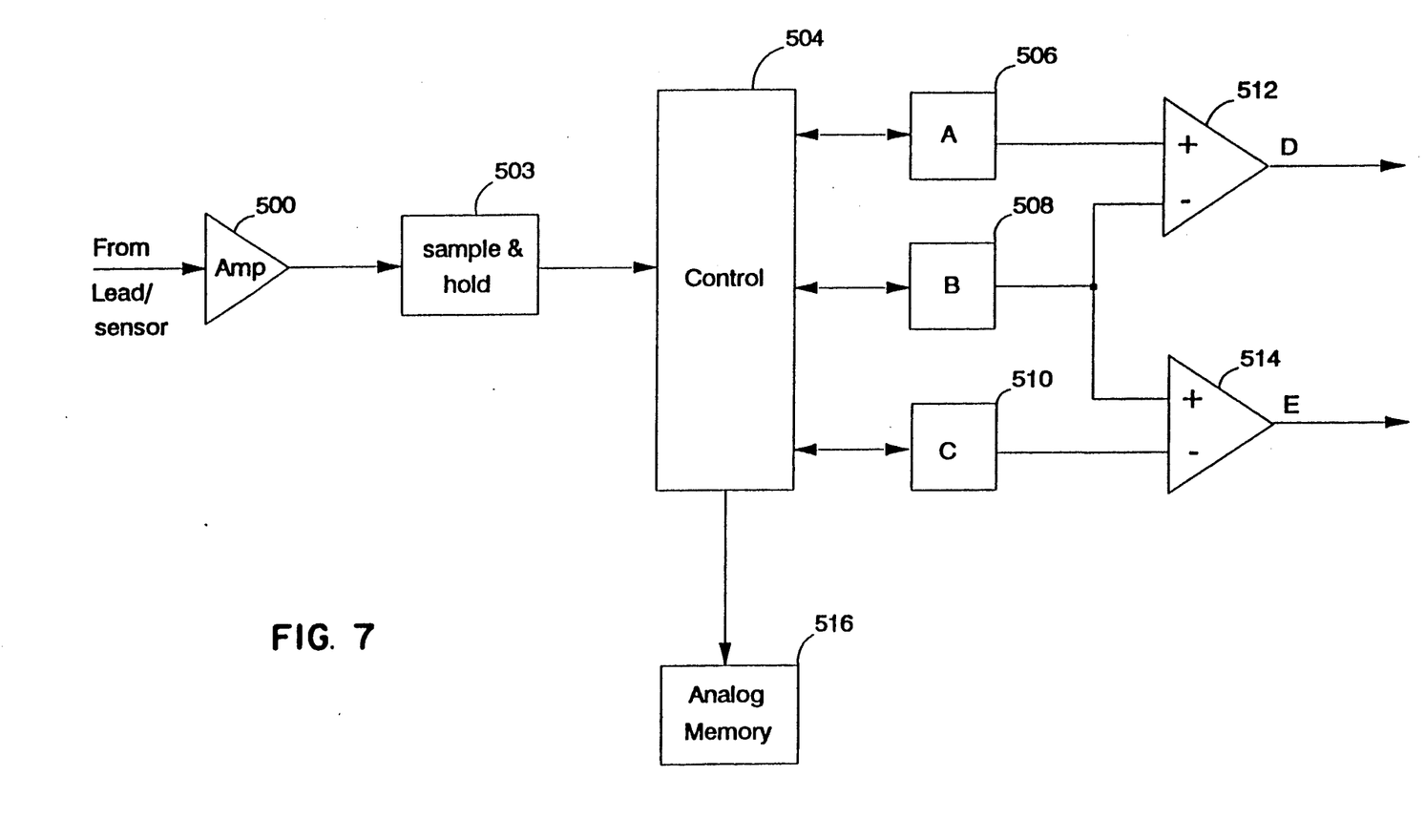
FIG. 7 is a diagram with an alternative mode of operation of the pacemaker of FIG. 2.

Finally turning to FIG. 7, a block diagram is shown which illustrates an alternative embodiment whereby the implantable device 10, FIG. 1, incorporates the storage and compression of analog data without the conversion of the analog data to digital data and the subsequent reconversion to analog data as described in the embodiment of FIG. 5. The signal to be stored may be one or both, the intracardiac signal from EGM amplifier 66 of FIG. 2 and/or the signal from a sensor such as the pressure sensor 22 shown in FIG. 2. A sample and hold circuit 502, sampled at a 128 Hz rate, generates analog voltage data that is stored temporarily in analog memory cells 506, 508, and 510 under control of MUX control circuit 504.

The first analog voltage value/data is stored in cell 510 and in the first memory location. The next two data samples are stored in cells 506 and 508, respectively. Comparator 512 compares the voltage level of analog cells 506 and 508 indicating, by a true logic level, if the voltage in cell 506 is greater than 508. Alternatively, a false logic level indicates that the voltage in cell 508 is greater than the voltage in cell 506. Similarly, comparator 514 compares the voltage level of analog cells 508 and 510 indicating by a true logic level if the voltage in cell 508 is greater than 510. Alternatively, a false logic level indicates that the voltage in cell 510 is greater than the voltage in cell 508. Microcomputer 32, FIG. 2, determines by a simple process flow, shown in FIG. 8, which value is stored in analog memory 516 by control/MUX circuit 504.

Figure 8:
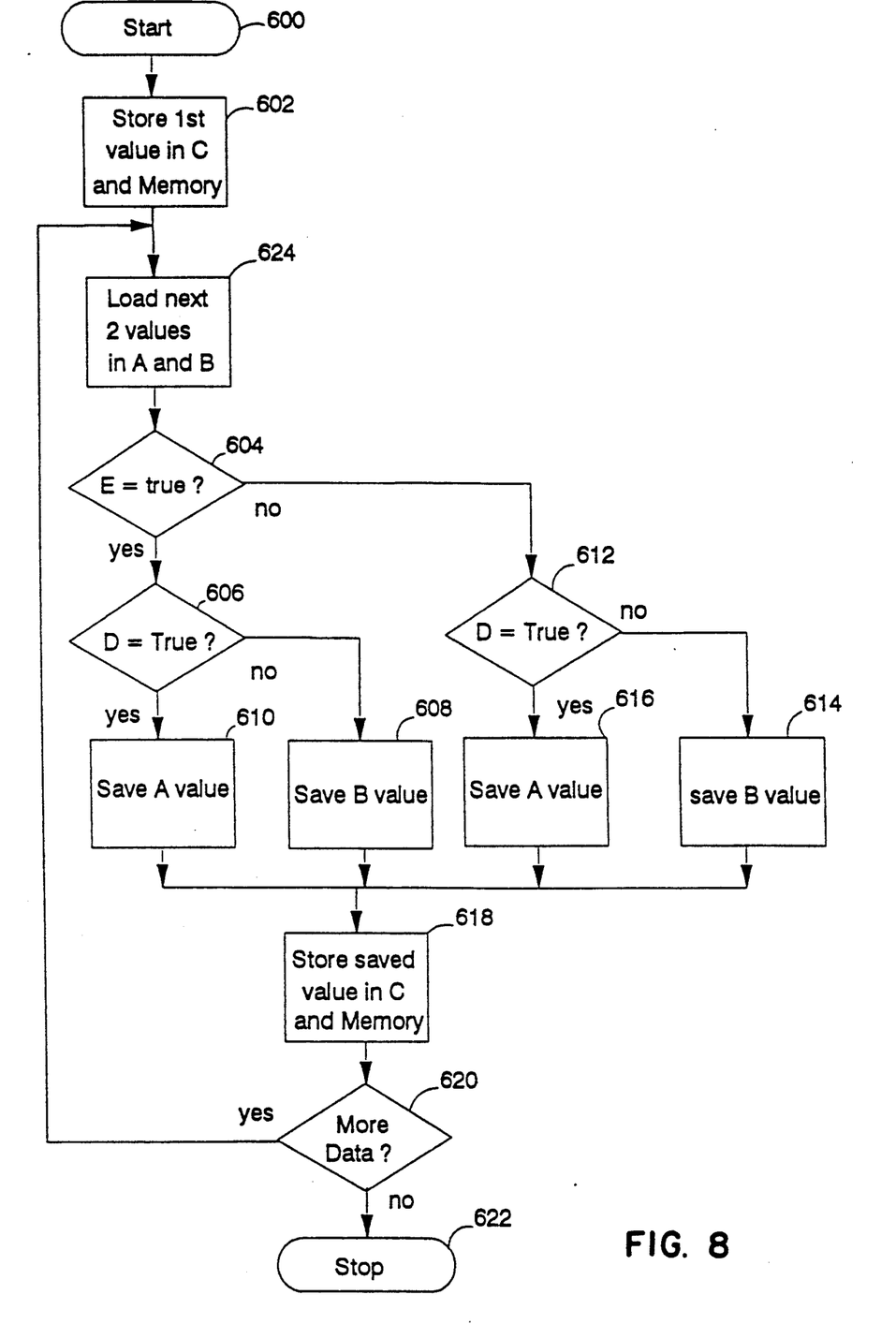
FIG. 8 is a flow diagram further illustrating the mode of operation of the pacemaker of FIG. 7.

Referring to FIG. 8, a block diagram is shown which illustrates a flow diagram associated with the compression of data from FIG. 7. The flow diagram of FIG. 8 begins by initiating the compression process at block 600 by event detection 104 of FIG. 3. The first data value (C) is stored in temporary cell 510 and the first address in memory in block 602. The next two values of data are stored in cells 508 (B) and 506 (A) respectively by block 624. If comparator 514 is 'TRUE' at block 604, the flow diagram tests if comparator 512 (D) is TRUE in block 606. If 'TRUE', the analog value stored in 506 is stored in memory and in cell 510 by block 618. If at block 606, comparator 514 (E) is 'FALSE', the analog value stored in cell 508 is stored in memory and cell 510 by block 618. If at block 604, comparator 514 is 'FALSE' and comparator 512 is 'TRUE', the analog value in cell 506 is stored in memory and cell 510 at block 618. If at block 612, comparator 512 is 'FALSE', the analog value stored in cell 508 is stored in memory and cell 510 by block 618. Block 620 tests for 2 more data values; if 'YES', the flow diagram returns to block 624. If 'NO', the compression process exits and stops at block 622.

After the analog signals are stored as herein above described, the analog data is converted to a signal for transmission to an external peripheral, such as a programmer, at a subsequent follow-up either via a clinic or hospital office visit or transtelephonically. Telemetry techniques are well known to those skilled in the art. Specific reference is made to converting the stored analog voltage to a pulse position modulated format as taught in Medtronic U.S. Pat. No. 4,556,063 to Thompson et. al, and incorporated herein by reference. Alternatively, the stored analog voltage may be digitized by an ADC and transmitted via the method taught in co-pending U.S. patent application Ser. No. 07/468,407 filed on Jan. 22, 1990, entitled "Improved Telemetry Format," which is assigned to the assignee of the present invention and which is incorporated herein by reference. The high data rate telemetry system of the '407 application would be a preferred method for transmitting the stored data to a peripheral allowing data to be stored at a low rate (e.g., 32 samples per second to even one sample per hour or per day) and transmitted to a peripheral at a very high rate.

Figure 9:
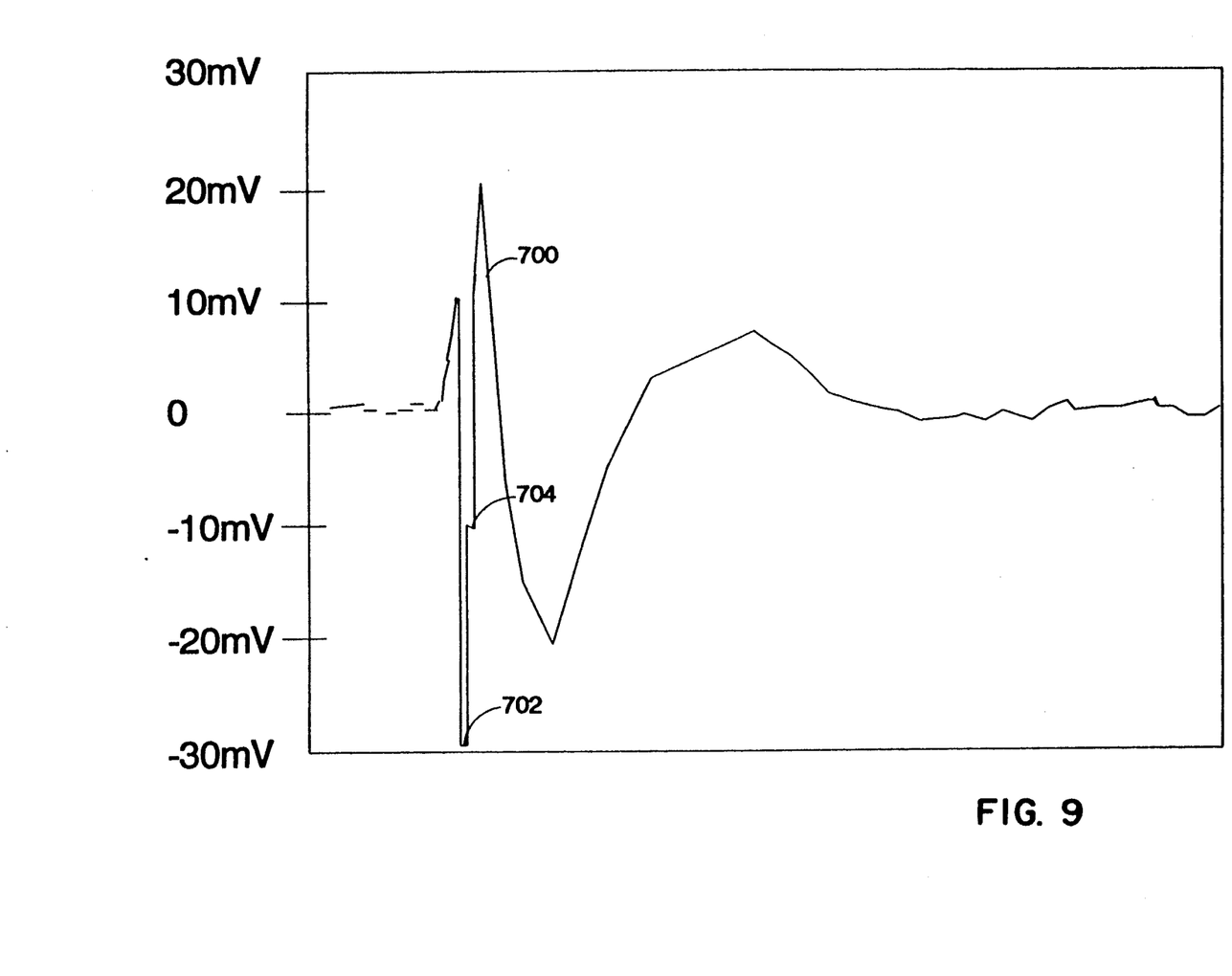
FIG. 9 is a diagram illustrating the analog voltage waveform stored in memory of the pacemaker of FIG. 2.
Figure 10:
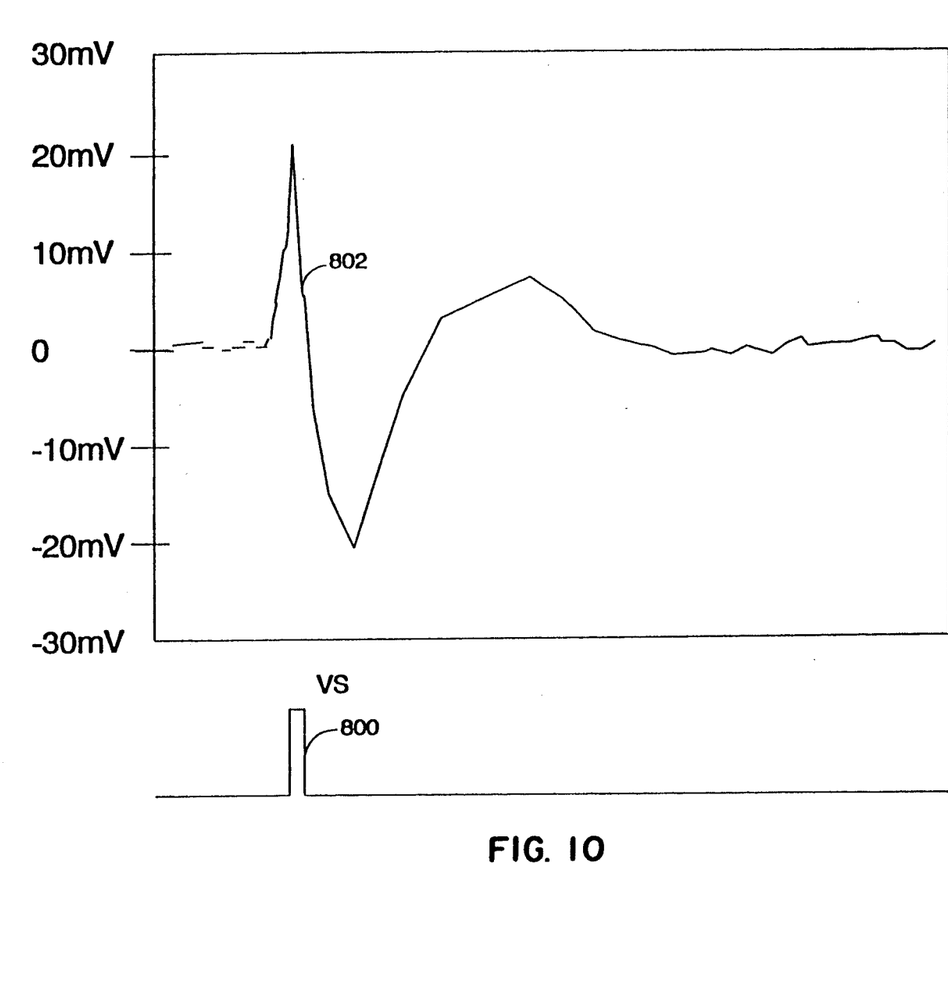
FIG. 10 is a diagram illustrating the display of an external programmer showing the reconstructed analog waveform of FIG. 9 simultaneous with a marker indicator of device function.

FIGS. 9 and 10 demonstrate the incorporation of marker or event indication information into the stored data. A marker indication of device function is entered into the stored analog data stream by utilizing a single bit indicator of $-V_{MAX}$ followed by a selectable voltage value indicating a marker of specific device function. In present day embodiments, intracardiac signal data is lost when digital marker information is simultaneously transmitted with the intracardiac signal because signal data bits are removed and replaced with digital data indicative of device function. FIG. 9 shows an example of the stored voltage 700 in the preferred embodiment of FIG. 3. At 702, the marker indicator of $-30$ mVolts ($-V_{MAX}$) is indicated. At 704, a value of $-10$ mVolts indicates a ventricular event. In a preferred embodiment for a dual chamber (DDD) pacemaker, the following are selectable voltage levels for data bit 704:

| Event | Voltage |
|---|---|
| $V_{Sense}$ | $-10$ mV |
| $V_{Refractory Sense}$ | $-20$ mV |
| $V_{Pace}$ | $-30$ mV |
| $A_{Sense}$ | $+10$ mV |
| $A_{Refractory Sense}$ | $+20$ mV |
| $A_{Pace}$ | $+30$ mV |

FIG. 10 shows the reconstructed and displayed EGM signal 802 with a ventricular sense ($V_{Sense}$) marker indicator 800 displayed on an external peripheral/programmer graphics screen or printed or plotted to a paper hardcopy. Note that the marker information has been removed from the analog data signal and the adjacent analog data points reconnected. Similarly, the time of occurrence of each stored event may be encoded and stored as herein described above.

In addition to the storage of analog data and subsequent telemetry to a programmer as taught herein above, a stored arrhythmia episode may be processed by microcomputer 32 to initiate a pacing, cardioversion or defibrillation therapy as is known in the art. Additionally, a stored signal indicative of capture, non-capture or a fusion beat may be compared on a periodic, or a beat-by-beat basis to the signal seen by the sense amplifier 64 after a pacing stimulus from output circuit 68. If an evoked response is not indicated (non-capture), the output stimulus pulse width and/or amplitude may be increased to regain capture as disclosed in U.S. Pat. No. 4,858,610 issued to Callaghan, et al., U.S. Pat. No. 4,878,497 issued to Callaghan, et al., and U.S. Pat. No. 4,729,376 issued to Decote, all of which are incorporated herein by reference in their entireties. The compression function may be performed by microcomputer 32 by pattern matching the periodic signal within a window from 5 to 80 mSec after output stimulus to the stored representation of the signal indicative of capture. Alternatively, the negative magnitude of the stored non-capture signal may be summed with the periodic signal with the resultant signal being indicative of an evoked response, if present.

From the foregoing detailed descriptions of particular embodiments of the invention, it should be apparent that a pacemaker has been disclosed which is provided with the capability of the compression and storing of a significant amount of analog data such as an intracardiac electrogram. While the particular embodiments of the present invention have been described herein in detail, it is to be understood that various alterations, modifications, and substitutions can be made therein without departing from the spirit and scope of the present invention, as defined in the claims, which follow.

We claim:

1. In a medical device encased in a housing and adapted for implantation within a patient's body having a monitoring system for recording electrical signals, said electrical signals having a level which varies over time as a function of a physiologic parameter of said patient, said monitoring system including means for sensing said electrical signal levels and means for periodically sampling said electrical signal at a periodic sample rate having predetermined intervals, the improvement comprising;

means for defining an analog voltage level indicative of said electrical signals, means for storing said analog voltage level, means for durably maintaining said analog voltage level and means for retrieving said voltage level.

2. An implantable medical device recited in claim 1, further comprising compression means coupled to said sampling means and to said storage means for compressing selected segments of said time varying signal levels and for providing a compressed signal output as a function thereof to said storage means.

3. An implantable medical device recited in claim 2, further comprising a control means coupled to said sensing means and said storage means, and wherein said compressing means comprises:

(a) Storage means for storing a first data value;
(b) Retrieving means for retrieving said first data value and a second subsequent data value;
(c) First evaluating means for determining if said first subsequent data value is greater than or equal to said first stored data value, if so, said larger of said first and second subsequent data value is saved;
(d) Second evaluating means for determining if said first subsequent data value is less than said first stored data value, if so, said smaller of said first and second subsequent data value is saved;

(e) Storage means to store said saved value; and (f) Said control means continuing with said retrieving, evaluating and storing for all data.

4. An implantable medical device recited in claim 1, further comprising event indication means coupled to said sensing means, said sampling means and said storage means for detecting predetermined variations of said time varying levels and for providing an event signal output to said storage means for storage in a desired timed relationship with said stored time varying signal levels.

5. An implantable medical device recited in claim 1, further comprising event detection means coupled to said sensing means, said sampling means and said storage means for detecting a predetermined sequence of events in said physiologic parameter of said patient and initiating said storage of said electrical signal levels.

6. An implantable medical device recited in claim 1, further comprising formatting means and telemetry transmitting means coupled to said storage means and receiving means external to said patient for transmitting said stored signal levels to said receiving means at a rate differing from said periodic sample rate.

7. An implantable medical device recited in claim 1, further comprising multiple storage means coupled to said sensing means and sampling means for storing a plurality of said time varying signal levels.

8. An implantable medical device recited in claim 7, further comprising a first memory monitoring and control means coupled to said storage means, said first memory monitoring and control means retaining said electrical signal levels until read and reset by subsequent interrogation by a programmer external to said patient.

9. An implantable medical device recited in claim 8, further comprising a second memory monitoring and control means coupled to said storage means, said second memory monitoring and control means for overwriting said stored signal levels of earlier occurring events such that the most recent events are retained until reset by subsequent interrogation by said external programmer.

10. An implantable medical device recited in claim 1, further comprising actuator means coupled to said sensing means, said sampling means and said storage means, said actuator means allowing said patient to initiate said storage of said electrical signal levels.

11. An implantable medical device recited in claim 10, wherein said actuator means comprises a reed switch closure recognizing means initiated by said patient placing a magnet in close proximity to said implantable medical device.

12. An implantable medical device recited in claim 10, wherein said actuator means comprises telemetry sensing means for detecting programming commands from an external programmer activated by said patient.

13. An implantable medical device recited in claim 9, wherein said actuator means comprises sensing means responsive to said patient tapping on said device housing to activate said storage of electrical signal levels.

14. An implantable medical device recited in claim 1, further comprising multiple sensing means coupled to said sampling means and storage means for simultaneously providing said electrical signal levels from a plurality of said physiologic parameters for simultaneous said storage.

15. An implantable medical device recited in claim 1, further comprising;

detection means for determining when said stored signal levels are indicative of arrhythmic events; and therapy means responsive to said detection means for delivery of said therapy to said patient's heart.

16. An implantable medical device recited in claim 1, further comprising;

polarization sensing means coupled to said sampling means and to said storage means for sensing a lead/tissue polarization voltage level after a pacing stimulus and generating a signal indicative of the occurrence or non-occurrence of a cardiac depolarization voltage level;

storage retrieving means for retrieving said generated signal indicative of the occurrence or non-occurrence of a cardiac depolarization voltage level;

evaluation means coupled to said polarization sensing means and to said storage retrieving means for determining if said signal indicative of said cardiac depolarization voltage level is present indicating that said pacing stimulus has evoked a cardiac response; and pacing control means for increasing the energy content of said pacing stimulus when said evaluation means determines said pacing stimulus has not evoked said cardiac response.

17. An implantable medical device recited in claim 16, said evaluation means further comprising;

a summing means for adding the negative of a stored signal indicative of said non-occurrence of a cardiac depolarization voltage level to said polarization sensing means; and evoked response determination means coupled to said summing means for determining if an evoked response has occurred.

18. An implantable medical device recited in claim 16, said evaluation means further comprising;

a window means beginning immediately after said pacing stimulus and continuing for a period of time where said evoked cardiac response would normally occur, said window is preferably from 5-80 mSec after said output stimulus.

19. An implantable medical device recited in claim 16, said evaluation means further comprising;

a waveform matching means for matching said stored signal indicative of said occurrence of a cardiac depolarization voltage level to said sensed lead/tissue polarization voltage level for determining if said evoked response has occurred.

* * * * *